(12) United States Patent
Boiteau et al.

(10) Patent No.: US 8,796,325 B2
(45) Date of Patent: Aug. 5, 2014

(54) METRONIDAZOLE ESTERS FOR TREATING ROSACEA

(75) Inventors: Jean-Guy Boiteau, Valbonne (FR); Jean-Michel Linget, Benfeld (FR)

(73) Assignee: Galderma Research & Development, Biot (FR)

( * ) Notice: Subject to any disclaimer, the term of this patent is extended or adjusted under 35 U.S.C. 154(b) by 31 days.

(21) Appl. No.: 13/807,167

(22) PCT Filed: Jun. 29, 2011

(86) PCT No.: PCT/EP2011/060925
§ 371 (c)(1), (2), (4) Date: Mar. 18, 2013

(87) PCT Pub. No.: WO2012/001055
PCT Pub. Date: Jan. 5, 2012

(65) Prior Publication Data
US 2013/0197048 A1    Aug. 1, 2013

(30) Foreign Application Priority Data
Jun. 29, 2010 (FR) .................... 10 55244

(51) Int. Cl.
*C07D 233/94* (2006.01)
*A61K 31/4164* (2006.01)

(52) U.S. Cl.
USPC ...................... 514/398; 548/330.1

(58) Field of Classification Search
USPC ...................... 514/398; 548/330.1
See application file for complete search history.

(56) References Cited

FOREIGN PATENT DOCUMENTS

WO    02/074290 A2    9/2002

OTHER PUBLICATIONS

Rao et al. "Synthesis, insecticidal and antifeedant activities of new type of pyrethroid esters." Indian J. Chem. 1990, 29B, 1034-1040.*
Dubey et al., "Evaluation of lipophilicity, antimicrobial activity and mutagenicity of some novel ester prodrugs of metronidazole," Indian Journal of Chemistry, 2009, pp. 1571-1576, vol. 48B.
Korting et al., "Current topical and systemic approaches to treatment of rosacea," Journal of the European Academy of Dermatology and Venereology, 2009, pp. 876-882, vol. 23.
Sobottka et al., "Rosazea 2009," Der Hautarzt, 2009, pp. 999-1009, vol. 12 (English language abstract included).

* cited by examiner

*Primary Examiner* — Samantha Shterengarts
*Assistant Examiner* — Amanda L Aguirre
(74) *Attorney, Agent, or Firm* — Dentons US LLP

(57) ABSTRACT

A compound of formula (I):

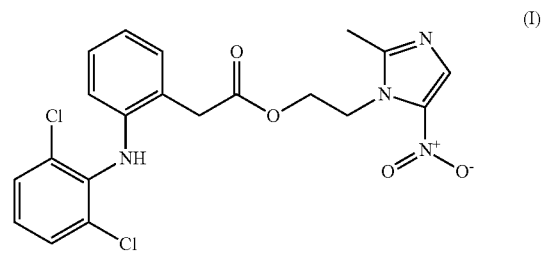

is described, as well as pharmaceutically acceptable salts thereof, and its use as a medicament.

12 Claims, No Drawings

METRONIDAZOLE ESTERS FOR TREATING ROSACEA

CROSS-REFERENCE TO PRIOR APPLICATIONS

This application is a National Stage of PCT/EP2011/060925, filed Jun. 29, 2011, and designating the United States (published in English on Jan. 5, 2012, as WO 2012/001055 A1), which claims priority to FR 10/55244, filed Jun. 29, 2010, each hereby expressly incorporated by reference in its entirety and each assigned to the assignee hereof.

The present invention relates to a compound of formula (I), and to its uses as a medicament, especially in the treatment and/or prevention of rosacea.

Rosacea is a progressive chronic common inflammatory dermatosis associated with vascular relaxation. It mainly affects the central part of the face and is characterized by reddening of the face or hot flushes, facial erythema, papules, pustules, telangiectasia and occasionally ocular lesions known as ocular rosacea. In serious cases, especially in men, the soft tissue of the nose may swell and produce a bulbous swelling known as rhinophyma. Rosacea develops over several years via episodes that are worsened by various stimuli such as temperature variations, alcohol, spices, exposure to sunlight, or emotions.

Rosacea is classified into four subtypes as a function of various clinical characteristics (Wilkin J. et al., JAAD, 2002, 46: 584-587).

The primary characteristics (histamine flushes, persistent erythema, papules and pustules, and telangiectasia) and secondary characteristics (burning or stinging sensation, plaques, dry appearance of the skin, oedema, ocular manifestations, phymatous changes) of rosacea are often observed in combination. The most common modes of exteriorization or combinations of signs are temporarily regrouped into specific subtypes, which are described below. Each category comprises the minimum number of signs that are sufficient to make a diagnosis of the corresponding subtype (although the modes of exteriorization are not necessarily limited to these signs), and it is possible that patients simultaneously present characteristics suggesting more than one subtype of rosacea.

Subtype 1: Erythematotelangiectasic Rosacea

Erythematotelangiectasic rosacea is characterized mainly by histamine flushes and persistent central facial erythema. The presence of telangiectasias is common, but not essential to the diagnosis of this subtype. A central facial oedema, burning and stinging sensations, and redness or desquamation are also occasionally observed. History of histamine flushes alone is common in the case of patients suffering from erythematotelangiectasic rosacea.

Subtype 2: Papulopustular Rosacea

Papulopustular rosacea is characterized by persistent central facial erythema and by transient papules and/or pustules distributed in the centre of the face. However, the papules and pustules may also affect the peri-orificial regions (i.e. the perioral, perinasal or periocular areas). The papulopustular subtype resembles common acne, but comedones are absent. Rosacea and acne may coexist, and, besides the papules and pustules resembling rosacea, the patients concerned will also possibly have comedones. Patients suffering from papulopustular rosacea occasionally complain of burning and stinging sensations.

This subtype is often observed before or at the same time as subtype 1 (including the presence of telangiectasias). The telangiectasias risk being masked by the persistent erythema and the papules or pustules.

Subtype 3: Phymatous Rosacea

Phymatous rosacea is manifested by thickening of the skin, nodules with an irregular surface and tumefaction. Rhinophyma is the commonest presentation, but phymatous rosacea may affect other regions, including the chin, the forehead, the cheeks and the ears. In the case of patients suffering from this subtype, the presence of enlarged and prominent follicular apertures is occasionally reported in the affected region, as are telangiectasias.

This subtype is often observed before or at the same time as subtype 1 or 2 (including the presence of persistent erythema, telangiectasias, papules and pustules). In the case of rhinophyma, these additional stigmata risk being particularly pronounced in the nasal region.

Subtype 4: Ocular Rosacea (or Ophthalmic Rosacea)

The diagnosis of ocular rosacea must be envisaged when a patient has one or more of the following ocular signs and symptoms: teary or bloodshot appearance (interpalpebral conjunctival hyperaemia), sensation of presence of a foreign body, of burning or stinging, dryness, itching, photosensitivity, blurred vision, telangiectasias of the conjunctiva and of the edge of the eyelid, or erythema of the eyelid and periocular erythema. Blepharitis, conjunctivitis and irregularity of the edges of the eyelid are other signs that may be detected. A chalazion or a chronic staphylococcic infection manifested by a stye and whose cause is a dysfunction of the meibomian glands is a frequent sign of ocular affection related to rosacea. Some patients complain of a reduction in visual acuity, which is due to corneal complications (punctuate keratitis, corneal infiltrates/corneal ulcers or marginal keratitis). By itself, the treatment of cutaneous rosacea may be without effect on the risk of lowering the visual acuity associated with ocular rosacea, and an ophthalmological approach will possibly be required.

Finally, other rarer forms of rosacea exist (variants), in particular granulomatous rosacea.

The diagnosis of ocular rosacea is most often made when cutaneous signs and symptoms are also detected. However, it is not necessary for cutaneous signs and symptoms to be present in order to make the diagnosis, and small-scale studies suggest that up to 20% of patients suffering from ocular rosacea may develop ocular signs and symptoms before cutaneous manifestations appear. Cutaneous lesions are the first to appear in the case of about half of these patients, and manifestations of the two types occur simultaneously in a minority of them.

Rosacea generally occurs between the ages of 25 and 70, and is much more common in people with fair complexion. It more particularly affects women, although this complaint is generally more severe in the case of men.

The pathogenesis of rosacea is poorly understood, and may involve several factors. These are, for example, vascular factors (abnormal vascular reactivity), immune factors, or alternatively exogenous factors such as the presence of follicular microorganisms such as bacteria and *Demodex folliculorum* mites (Diamantis S. & Waldorf H. A., *J. Drug Dermatol.*, 2006, 5: 8-12; Wilkin J. K., Arch. *Dermatol.*, 1994, 130: 359-362; Buechner S. A., *Dermatology*, 2005, 210: 100-108).

Conventionally, rosacea is treated orally or topically. Among the agents having a marketing authorization for the "rosacea" indication are topical metronidazole and oral doxycycline (Cribier B., La rosacée, Masson-Eticom, Paris, 2002).

Long-term oral treatments with tetracycline derivatives are problematic for many reasons, in particular on account of their significant side effects. The oral administration of tetracyclines, especially doxycycline, may induce photosensitivity, or even phototoxicity at and above 100 mg/day (Layton A.

M., Cunliffe W. J. Phototoxic eruptions due to doxycycline-a dose-related phenomenon. *Clin. Exp. Dermatol.* 1993; 18:425-427), or alternatively gastrointestinal disorders (Maibach H. Second-generation tetracyclines, a dermatologic overview: clinical uses and pharmacology. *Cutis.* 1991; 48:411-417).

In addition, these treatments do not make it possible to effectively treat and/or prevent all of the symptoms associated with rosacea. Considering the chronic nature of rosacea, with a typical profile of remission and exacerbation, an ideal treatment requires use that may be prolonged, in a safe and effective manner.

Patent application WO 02/74290 describes the use of at least one non-steroidal anti-inflammatory drug (NSAID) for treating rosacea. This compound may especially be piroxicam, aspirin, ibufenac or naproxen. It may optionally be used in combination with a nitroimidazole. The simultaneous use of an NSAID and of a nitroimidazole has, however, appreciable side effects, especially gastrointestinal and renal effects associated with the use of metronidazole as nitroimidazole (D. I. Edwards, *Br. J. Vener. Dis.* 1980; 56: 285-290), or ulcers associated with the use of an NSAID (C. J. Hawkey, *J. Rheumatology,* 2002; 29: 4; 650-652).

There is thus a need for active agents that are effective for treating rosacea, which can be used for long periods, and which have the least possible side effects.

The aim of the present invention is thus to propose an effective treatment for rosacea, which especially reduces the side effects for the patient. Preferably, this treatment is performed topically, which considerably reduces any systemic side effect.

One subject of the present invention is thus a compound chosen from the compound of formula (I) below:

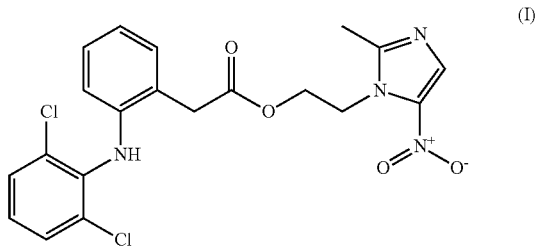 [SMILES: Cc1ncc([N+](=O)[O-])n1CCOC(=O)Cc1ccccc1Nc1c(Cl)cccc1Cl]

(I)

and pharmaceutically acceptable salts thereof.

The compound of formula (I) has the chemical name 2-(2-methyl-5-nitroimidazol-1-yl)ethyl [2-(2,6-dichlorophenylamino)phenyl]acetate.

This compound contains an ester function, which is specifically cleaved in keratinocytes, as is demonstrated in Example 1. For comparative purposes, other metronidazole esters with NSAIDs, for instance indomethacin, niflumic acid, diflunisal or ketorolac esters, were prepared and tested on keratinocyte cultures. All these compounds are stable in the presence of keratinocytes, unlike the compound of formula (I) according to the invention.

This particular instability of the compound of formula (I) and of pharmaceutically acceptable salts thereof is thus surprising and unexpected. Without wishing to be bound by any theory, it is quite likely that this particular surprising instability of the compound of formula (I) and of pharmaceutically acceptable salts thereof makes it possible to obtain the antirosacea activity once the compound of formula (I) or the pharmaceutically acceptable salts thereof has (have) penetrated the skin and become hydrolysed on contact with the keratinocytes.

The present invention also relates to a compound chosen from the compound of formula (I) and pharmaceutically acceptable salts thereof, for its use as a medicament.

A subject of the present invention is also a compound chosen from the compound of formula (I) and pharmaceutically acceptable salts thereof, for its use in the treatment and/or prevention of rosacea.

A subject of the present invention is also the use of at least one compound chosen from the compound of formula (I) and pharmaceutically acceptable salts thereof, for preparing a medicament for treating and/or preventing rosacea.

The term "salts of the compound of formula (I) according to the invention" means salts of this compound with a pharmaceutically acceptable acid.

The pharmaceutically acceptable acid is especially:
a pharmaceutically acceptable inorganic acid, for instance hydrochloric acid, sulfuric acid, phosphoric acid, nitric acid or hydrobromic acid;
or a pharmaceutically acceptable organic acid, for instance acetic acid, tartaric acid, maleic acid, hydroxymaleic acid, fumaric acid, citric acid, lactic acid, mucic acid, gluconic acid, benzoic acid, succinic acid, oxalic acid, phenylacetic acid, methanesulfonic acid, toluenesulfonic acid, benzenesulfonic acid, salicylic acid, aspartic acid, glutamic acid and ascorbic acid.

Preferably, the salts of the compound of formula (I) are chosen from the hydrochloride, the citrate, the salicylate and the benzoate of the compound of formula (I).

Even more preferentially, the salt of the compound of formula (I) is 2-(2-methyl-5-nitroimidazol-1-yl)ethyl [2-(2,6-dichlorophenylamino)phenyl]acetate hydrochloride.

The term "treatment" or "treating" rosacea means reducing and/or inhibiting the development of rosacea and/or of the symptoms thereof.

The term "prevention" or "preventing" rosacea means reducing and/or avoiding the appearance of the symptoms of rosacea.

The term "compound according to the invention" means, indiscriminantly, the compound of formula (I) and/or a pharmaceutically acceptable salt thereof.

The compound according to the invention may be prepared according to the process described in Example 2.

The compound chosen from the compound of formula (I) and pharmaceutically acceptable salts thereof may thus be formulated in pharmaceutical compositions for human use. The said compositions comprise, in a pharmaceutically acceptable medium, at least one compound chosen from the compound of formula (I) and pharmaceutically acceptable salts thereof.

The term "pharmaceutically acceptable medium" means a medium that is compatible with the skin, mucous membranes and the integuments.

The pharmaceutical composition that may be used according to the invention may be administered topically, parenterally or orally.

Preferably, the compound chosen from the compound of formula (I) and pharmaceutically acceptable salts thereof is present in a pharmaceutical composition for topical application.

The term "topical application" means application to the skin, mucous membranes and/or the integuments.

The composition according to the invention comprises from 0.001% to 10% by weight of compound(s) according to the invention relative to the total weight of the composition.

Preferentially, the composition according to the invention contains from 0.1% to 5% by weight of compound(s) according to the invention relative to the total weight of the composition.

The topical pharmaceutical composition may be in liquid, pasty or solid form, and more particularly in the form of an ointment, a cream, a milk, a pomade, a powder, an impregnated pad, a syndet, a wipe, a solution, a gel, a spray, a mousse, a suspension, a lotion, a stick, a shampoo or a washing base. It may also be in the form of a suspension of microspheres or nanospheres or lipid or polymer vesicles or a polymer patch and a hydrogel allowing controlled release. This pharmaceutical composition for topical application may be in anhydrous form, in aqueous form or in the form of an emulsion.

In one preferred variant of the invention, the pharmaceutical composition for topical application is in the form of a solution, a gel or an emulsion.

Such pharmaceutical compositions may be manufactured according to processes that are well known to those skilled in the art.

Various examples of preparation and use of the compounds according to the invention will now be given, for illustrative purposes and with no limiting nature.

EXAMPLES

Example 1

Stabilities Evaluated on Keratinocyte Cultures

The stability on keratinocyte cultures is evaluated using human neonatal keratinocytes (Cell'N Tech) cultured in a 75 cm² flask and detached at 90-100% of confluence with vegetable trypsin (trypLE GIBCO). The compound of formula (I) was tested at 2 μM in the medium CNT-057 (Cell'N Tech) supplemented with 0.1% pluronic acid in 24-well plates. The final DMSO concentration is 0.1%. Degradation kinetics are performed with a Tecan EVO robot over 24 hours. The samples taken are then assayed by LC/MS/MS (Micromass) in comparison with a calibration range of the test product, prepared under the same conditions as the samples (⅓ culture medium and ⅔ methanol). The chromatographic conditions are optimized for each product. An assay of the appearance of metronidazole is also performed using these same samples.

The half-life time ($t_{1/2}$) of the compound of formula (I) is 8 hours.

For comparative purposes, the metronidazole esters with indomethacin, niflumic acid, diflunisal or ketorolac do not become hydrolysed on the keratinocyte cultures.

Example 2

Synthesis of 2-(2-methyl-5-nitroimidazol-1-yl)ethyl [2-(2,6-dichlorophenylamino)phenyl]acetate 191 mg (1.0 mmol, 1 eq.) of 1-(3-dimethylaminopropyl)-3-ethylcarbodiimide are added to a mixture of 318 mg (1.0 mmol, 1 eq.) of sodium [2-(2,6-dichlorophenylamino)phenyl]acetate and 171 mg (1.0 mmol, 1 eq.) of metronidazole in 10 mL of dichloromethane in the presence of 6 mg (0.05 mmol, 0.05 eq.) of 4-dimethylaminopyridine. The reaction medium is stirred for 18 hours at room temperature. The reaction medium is treated with water and extracted with dichloromethane. The organic phases are combined, dried over magnesium sulfate and evaporated. The residue is chromatographed on silica gel (AnaLogix SF15-24g, Spot II column) eluted with heptane/ethyl acetate (gradient).

250 mg of 2-(2-methyl-5-nitroimidazol-1-yl)ethyl [2-(2,6-dichlorophenylamino)phenyl]acetate are obtained in the form of an off-white solid. (m.p.=122-124° C.). Yield=56%.

¹H NMR (CDCl₃, 400 MHz): 2.26 (s, 3H); 3.70 (s, 2H); 4.43 (m, 2H); 4.50 (m, 2H); 6.46 (d, J=8 Hz, 1H); 6.53 (s, 1H) 6.91 (m, 2H); 7.07 (m, 2H); 7.27 (d, J=8 Hz, 2H); 7.86 (s, 1H)

¹³C NMR (CDCl₃, 400 MHz): 14.0; 38.4; 45.0; 63.3; 118.3; 122.3; 123.4; 124.3; 128.4; 128.9; 129.5; 130.9; 133.1; 137.5; 142.6; 150.9; 171.7.

The invention claimed is:

1. A compound formula (I) below:

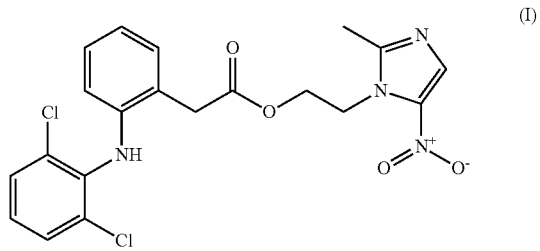

or a pharmaceutically acceptable salt thereof.

2. The compound as defined in claim 1, wherein the compound is incorporated into a medicament.

3. The compound as defined in claim 1, wherein the compound is effective in treating rosacea.

4. The compound as defined in claim 1, wherein the salt of the compound of formula (I) is a salt of the compound with a pharmaceutically acceptable acid.

5. The compound as defined in claim 1, wherein the pharmaceutically acceptable acid is selected from the group consisting of:
   a) pharmaceutically acceptable inorganic acid; and
   b) a pharmaceutically acceptable organic acid.

6. The compound as defined in claim 1, wherein the compound is selected from the group consisting of a compound of formula (I), a hydrochloride of the compound of formula (I), a citrate of the compound of formula (I), a salicylate of the compound of formula (I) and a benzoate of the compound of formula (I).

7. The compound as defined in claim 1, wherein the compound is 2-(2-methyl-5-nitroimidazol-1-yl)ethyl [2-(2,6-dichlorophenylamino)phenyl]acetate.

8. A pharmaceutical composition for topical application comprising a compound as defined in claim 1 and a pharmaceutical carrier.

9. The composition as defined in claim 8, said composition being in the form of a solution, a gel or an emulsion.

10. The composition as defined in claim 8, wherein the compound is present in an amount of 0.001% to 10% by weight relative to the total weight of the composition.

11. The compound as defined in claim 5, wherein the pharmaceutically acceptable inorganic acid is selected from the group consisting of hydrochloric acid, sulfuric acid, phosphoric acid, nitric acid and hydrobromic acid.

12. The compound as defined in claim 5, wherein the pharmaceutically acceptable organic acid is selected from the group consisting of acetic acid, tartaric acid, maleic acid, hydroxymaleic acid, fumaric acid, citric acid, lactic acid, mucic acid, gluconic acid, benzoic acid, succinic acid, oxalic acid, phenylacetic acid, methanesulfonic acid, toluenesulfonic acid, benzenesulfonic acid, salicylic acid, aspartic acid, glutamic acid and ascorbic acid.

* * * * *